(12) United States Patent
Owen et al.

(10) Patent No.: US 7,845,149 B2
(45) Date of Patent: Dec. 7, 2010

(54) TUBE CAPPER/DECAPPER

(75) Inventors: Stephen Owen, Cambridgeshire (GB);
Justin Owen, Hertfordshire (GB);
Adrian Neil Bargh, Hertfordshire (GB)

(73) Assignee: The Automation Partnership (Cambridge) Limited, Royston, Hertfordshire (GB)

(*) Notice: Subject to any disclaimer, the term of this patent is extended or adjusted under 35 U.S.C. 154(b) by 130 days.

(21) Appl. No.: 11/780,526

(22) Filed: Jul. 20, 2007

(65) Prior Publication Data

US 2008/0022808 A1    Jan. 31, 2008

(30) Foreign Application Priority Data

Jul. 26, 2006   (EP)   .................... 06117864

(51) Int. Cl.
*B65B 7/28* (2006.01)
(52) U.S. Cl. .............. 53/490; 53/485; 53/281
(58) Field of Classification Search .......... 53/484, 53/490, 276, 281, 285, 286, 287, 299, 300, 53/305, 308, 309, 317, 318, 319, 381.1
See application file for complete search history.

(56) References Cited

U.S. PATENT DOCUMENTS

| 2,760,391 | A |   | 8/1956 | Knutson |
| 3,483,997 | A |   | 12/1969 | Ritter |
| 3,589,103 | A |   | 6/1971 | Calvillo et al. |
| 3,899,864 | A | * | 8/1975 | Uchida et al. .......... 53/212 |
| 3,908,812 | A | * | 9/1975 | Graff .......... 198/418.1 |
| 4,178,732 | A |   | 12/1979 | Pfleger |
| 4,277,932 | A | * | 7/1981 | Campbell .......... 53/497 |
| 5,425,402 | A | * | 6/1995 | Pringle .......... 141/235 |
| 5,860,889 | A | * | 1/1999 | Schlosser et al. .......... 475/221 |
| 6,105,343 | A |   | 8/2000 | Grove |
| 6,216,340 | B1 |   | 4/2001 | Fisbind |
| 2003/0041560 | A1 |   | 3/2003 | Kemintz |
| 2006/0130597 | A1 |   | 6/2006 | Bernard |

FOREIGN PATENT DOCUMENTS

| DE | 2132244 | 4/1973 |
| DE | 4232619 | 3/1994 |
| GB | 2010789 | 7/1979 |
| WO | WO2006/029083 | 3/2006 |
| WO | WO2006/072143 | 7/2006 |

* cited by examiner

*Primary Examiner*—Rinaldi I. Rada
*Assistant Examiner*—Lindsay Low

(57) ABSTRACT

A capper/de-capper system 1 has a rack support 10 for supporting a rack 11 containing a plurality of capped tubes 31 in a given position. A head unit 12 supports a two-dimensional array of capping/de-capping spindles 13, each of which includes a clutch 133 and a capping/de-capping spigot 131 or socket, the spindles being aligned with the tube positions defined in the rack. A drive mechanism 108 moves the tubes and the head unit relatively towards and away from one another in use, when a rack containing capped tubes is disposed in the rack support, causing engagement and disengagement of the capping/de-capping spigots or sockets with and from the tube caps 32. A spindle drive system 15-22 provides simultaneous rotation of the capping/de-capping spigots or sockets together after engagement with the caps, either to detach caps from the tubes or attach caps to the tubes.

14 Claims, 19 Drawing Sheets

US 7,845,149 B2

TUBE CAPPER/DECAPPER

BACKGROUND

The present invention relates to a capper/de-capper device and method for attaching and removing caps from tubes, and, more particularly, a device and method for removing screw-threaded caps from tubes such as microtubes used in laboratories or micro-biological systems.

High value biological samples are often stored and processed using so-called SBS format racks containing a plurality of tubes. Such racks may contain, for example, 96 tubes in an array of 8 by 12 apertures designed to hold the tubes securely. The tubes and their contents may be manoeuvred in a processing system, for example between a cold store and various processing stations and may be required to be filled (partly or fully) or processed simultaneously or individually.

Conventionally, capping/de-capping has either been carried out by hand or else by means of a capping/de-capping unit individually engageable with the tubes either while they are still held in the rack or else after they have been separated from the rack. This is not only tedious (in the case of manual capping/de-capping), but also slow as it is usual for plural tubes to require processing in the same way at the same time.

It is known to provide a linear array of cappers/de-cappers to allow capping/de-capping of a row of tubes, but such systems have been bulky as a result of the dimensions of the drive mechanisms of the capper/de-cappers, the close spacing of the tubes requiring the drive mechanisms of the cappers/de-cappers to be remote from the capper/de-capper heads and disposed over a larger footprint than the rack because of their size.

The present invention is aimed at overcoming these problems and providing a capper/de-capper which can cap or de-cap a two-dimensional array of tubes simultaneously.

SUMMARY OF THE INVENTION

According to the present invention therefore a capper/de-capper system comprises
- a rack support for supporting a rack containing a plurality of capped tubes in a given position;
- a head unit supporting a two-dimensional array of capping/de-capping spindles, each including a clutch and a capping/de-capping spigot or socket, the spindles being aligned with the tube positions defined in the rack;
- a drive mechanism for moving the tubes and head unit relatively towards and away from one another in use, when a rack containing capped tubes is disposed in the rack support, to cause engagement and disengagement of the capping/de-capping spigots or sockets with and from the tube caps; and
- a spindle drive system for causing simultaneous rotation of the capping/de-capping spigots or sockets together after engagement with the caps, either to detach caps from the tubes or attach caps to the tubes.

A particular advantage of the clutch system of the capper/de-capper and method according to the invention is that, regardless of the number of tubes disposed in a given rack, the same capping torque can be applied to all caps.

The tubes may be arranged, in use, to be moved towards or away from the head unit. Preferably, the rack support is driven upwardly and downwardly, but alternatively, the head unit may be movable towards or away from the tubes in use.

The spindle drive system preferably includes a drive plate arranged to be movable upwardly and downwardly with respect to the spindles and in screw-threaded engagement therewith to cause simultaneous rotation of the spindles on movement relative thereto.

The clutch on each spindle is preferably a spring-wrap clutch. Alternatively, the clutch on each spindle may comprise a pair of toothed dogs arranged to slip in one direction when the torque exceeds a given limit overcoming the spring-loading.

The rack support may include a plurality of locking pins engageable with individual ones of the tubes in a rack in use, to hold the tubes in fixed position within the rack.

The locking pins may be engageable upwardly through the rack support and rack into engagement with the tubes.

The invention also includes a method of de-capping a plurality of tubes disposed in a rack, the method comprising
- placing a rack containing a plurality of capped tubes on a rack support at a given position;
- moving the rack support and a head unit supporting a two-dimensional array of capping/de-capping spindles, each including a clutch and a capping/de-capping spigot or socket, relatively towards one another to cause engagement of the capping/de-capping spigots or sockets with the tube caps; and thereafter
- causing simultaneous rotation of the capping/de-capping spigots or sockets together to detach the caps from the tubes.

The invention also includes a method of capping a plurality of tubes disposed in a rack, the method comprising
- placing a rack containing a plurality of capped tubes on a rack support at a given position;
- moving the rack support and a head unit supporting a two-dimensional array of capping/de-capping spindles, each including a clutch and a capping/de-capping spigot or socket holding a tube cap, relatively towards one another to cause engagement of the tube caps with the tubes; and thereafter
- causing simultaneous rotation of the capping/de-capping spigots or sockets together and with the caps to attach the caps to the tubes.

BRIEF DESCRIPTION OF THE DRAWINGS

Two examples of a capper/de-capper device according to the present invention will now be described with reference to the accompanying drawings in which FIGS. 1 to 17 of show an elevation of a first exemplary system at various stages during a possible operating cycle.

DETAILED DESCRIPTION

Figure 1:
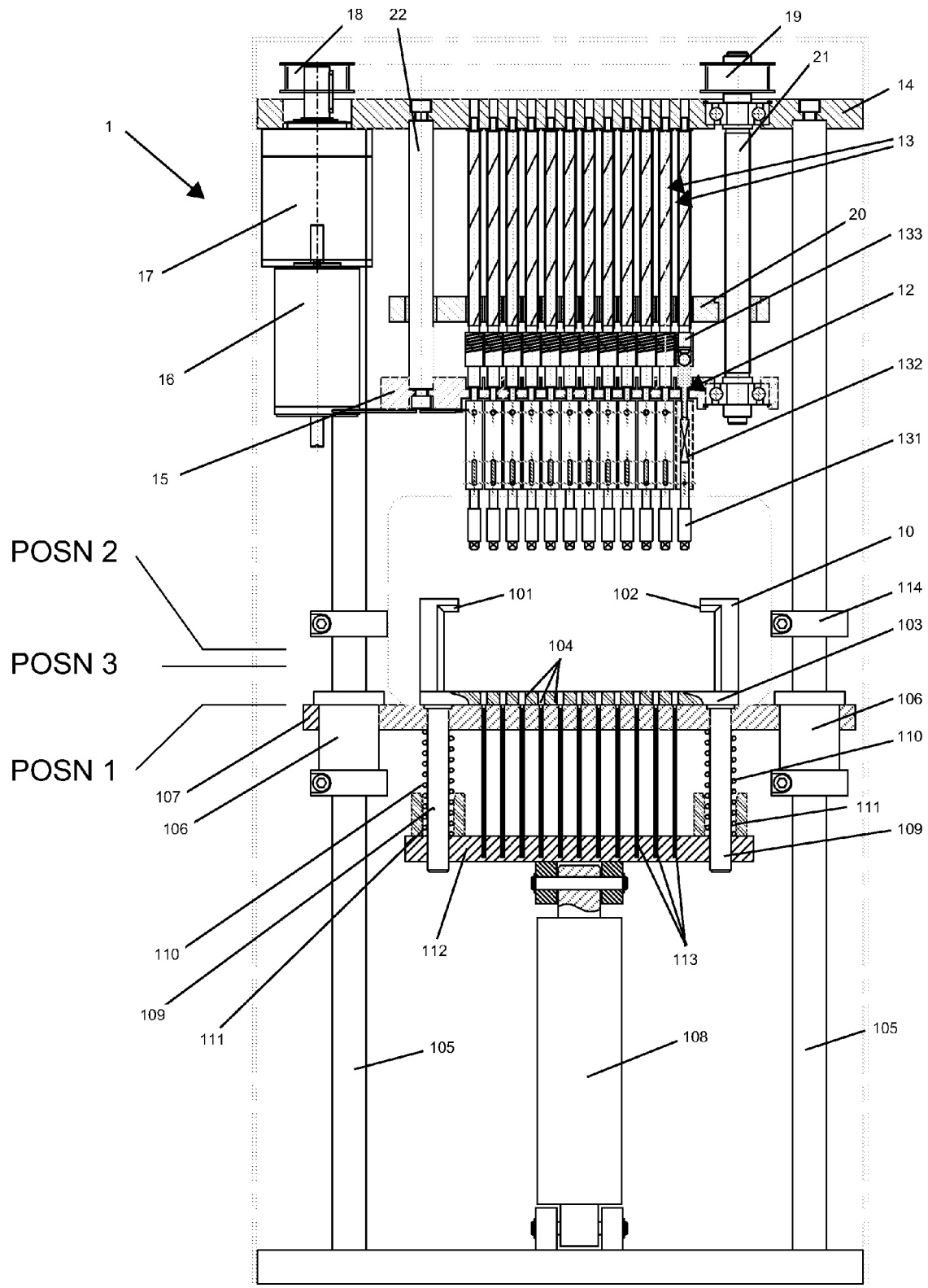

The capper/de-capper system 1 shown in the drawings comprises a standalone system for capping and uncapping screw-cap tubes and is designed as a bench-top system for use in either a laboratory or within a micro-biological control cabinet.

The system 1 includes a rack support 10 which is dimensioned, in this example, specifically to receive a standard 96-well SBS format rack 11 (see FIG. 2) in a defined and fixed horizontal position relative to a head unit 12.

The head unit 12 includes 96 capping/de-capping spindles 13 arranged in an 8 by 12 two-dimensional array.

Figure 18:
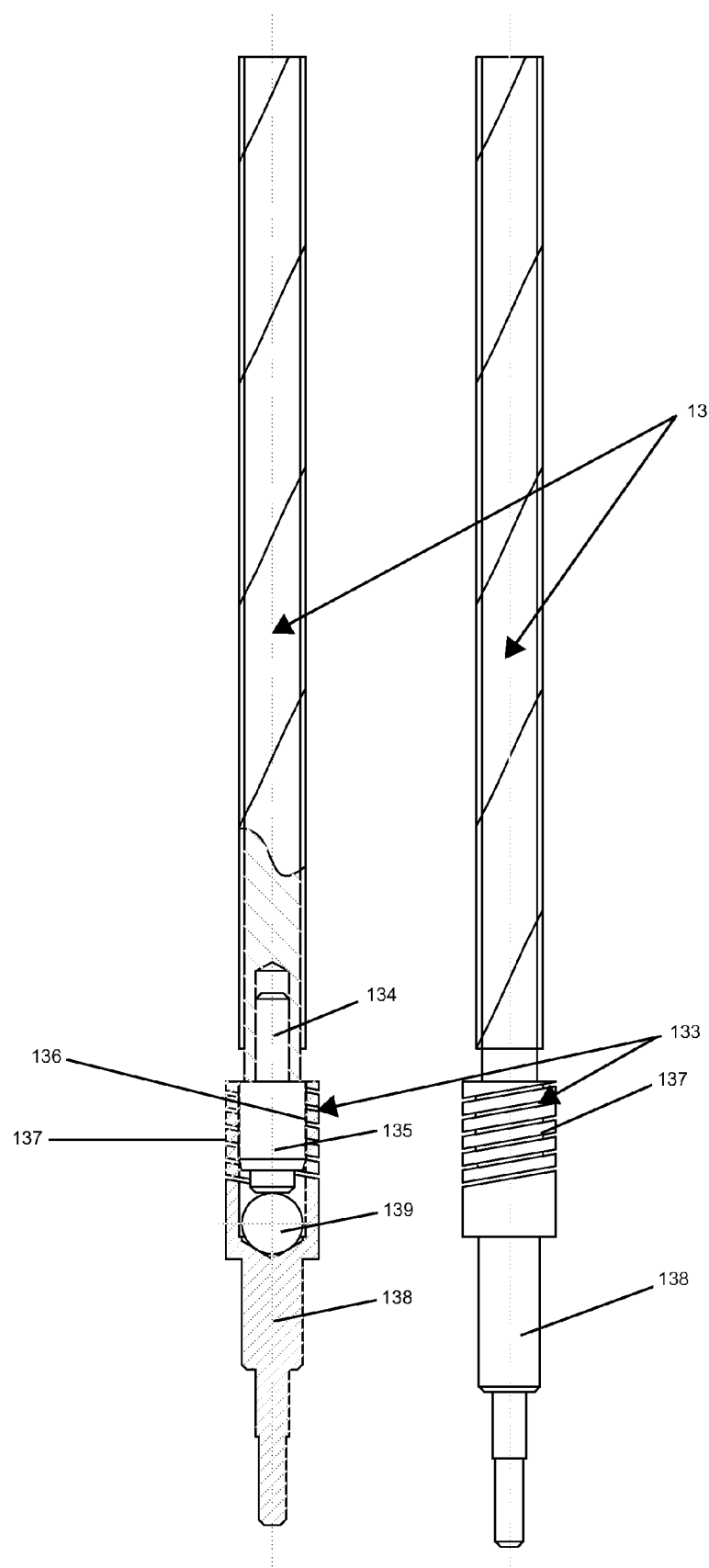
FIG. 18 shows the top part of a pair of adjacent spindles, one partially sectioned, in further detail.

FIG. 18 is series of views of one of the spindles 13 shown in more detail. It can be seen that the spindle 13 includes a capper/de-capper spigot 131 which is spring-loaded by a compression spring 132 and rotatably driven through a clutch 133. Each of the clutches 133 may comprise a spring wrap clutch as shown in FIG. 18, but various alternatives are possible and, for example, the clutch may comprise a pair of spring-loaded toothed dogs arranged to slip when the torque exceeds a given limit overcoming the spring-loading.

In the spring wrap clutch 133 shown in the present drawings, a drive shaft 134 has a drive wheel 135 which is disposed as a friction fit within a socket 136 formed internally of a helical spring 137 which is integrally formed with a driven shaft 138, the opposite end of which is in driving engagement with the capper/de-capper spigot 131. A spherical bearing 139 disposed in the socket 136 provides a low-friction end stop for the end of the drive wheel 135. When the drive wheel 135 rotates in one direction (for de-capping) the spring tightens against the drive wheel 135 to apply a higher torque than when it rotates in the opposite direction (for capping), when it loosens and slips when a lower, given torque is exceeded. The use of individual clutches ensures that each cap is tightened to the desired given torque to ensure that, on re-capping, the caps can be tightened to a torque, typically say 0.06 to 0.1 Nm, at which the tubes can be sure of being properly sealed.

The head unit 12 mounts all 96 capping/de-capping spindles 13 by means of upper and lower bearing plates 14, 15. The spindles 13 are rotatable together under the action of a motor 16 driving, via a gearbox 17, pulleys 18 and 19 and a belt (not shown), a pair of drive shafts 21 (one at opposed corners of the top of the head unit) which are engaged with a drive plate 20 to drive the spindles 13. To ensure that the drive plate 20 does not tilt, the alternate opposed corners slide on bearings along support shafts 22. The drive plate 20 has threaded apertures in screw-threaded engagement with the drive shafts 21 and moves up and down as the shafts 21 rotate in one direction or the other. Similarly, the spindles 13 have a 'fast' screw thread and are in screw-threaded engagement with the other apertures in the drive plate 20 so that, as it is driven downwards, the spindles 13 rotate anti-clockwise and as it is driven upwards they rotate clockwise.

The rack support 10 includes shoulders 101, 102 and a base plate 103 having a series of apertures 104, the purpose of which will be described later. The rack support is mounted for vertical sliding movement between three positions (POSN1, POSN2, POSN3) on shafts 105, via sliding bearings 106 and a driven plate 107, under the action of an electrically driven linear actuator 108 engaged with the driven plate 107 via a pair of support shafts 109 which have surrounding compression springs 110 mounted in retaining cups 111 on a second drive plate 112.

The second drive plate 112 includes upwardly extending locking pins 113, one aligned with each aperture 104 in the base plate 103 of the rack support 10, for use as described below.

Figure 2:
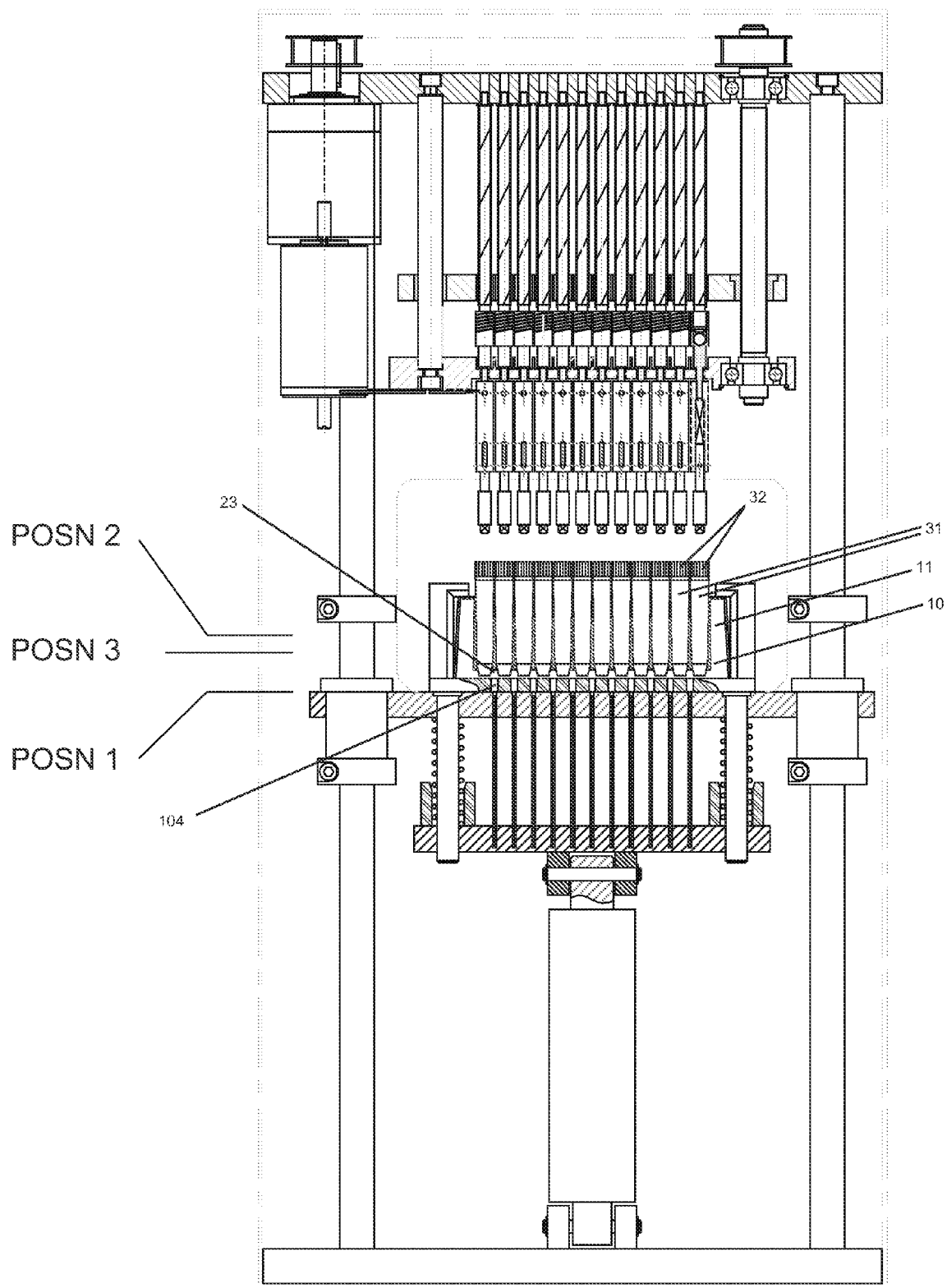

At the start of operation of a de-capping cycle, the system components are in the positions shown in FIG. 1. The rack support 10 is empty and is in its lowermost position POSN1. An operator (or a robot arm if the apparatus is used in an automated system) inserts a rack 11 into the rack support 10 as shown in FIG. 2, the rack support 10 defining the horizontal position of the rack 11 so that each tube 31 is vertically aligned with a corresponding spindle 13 of the head unit 12. As can be seen from FIG. 2, each tube 31 includes a screw-threaded cap 32 and the bottom of the rack has corresponding apertures 23 which are aligned with the apertures 104 in the rack support base plate 103.

Figure 3:
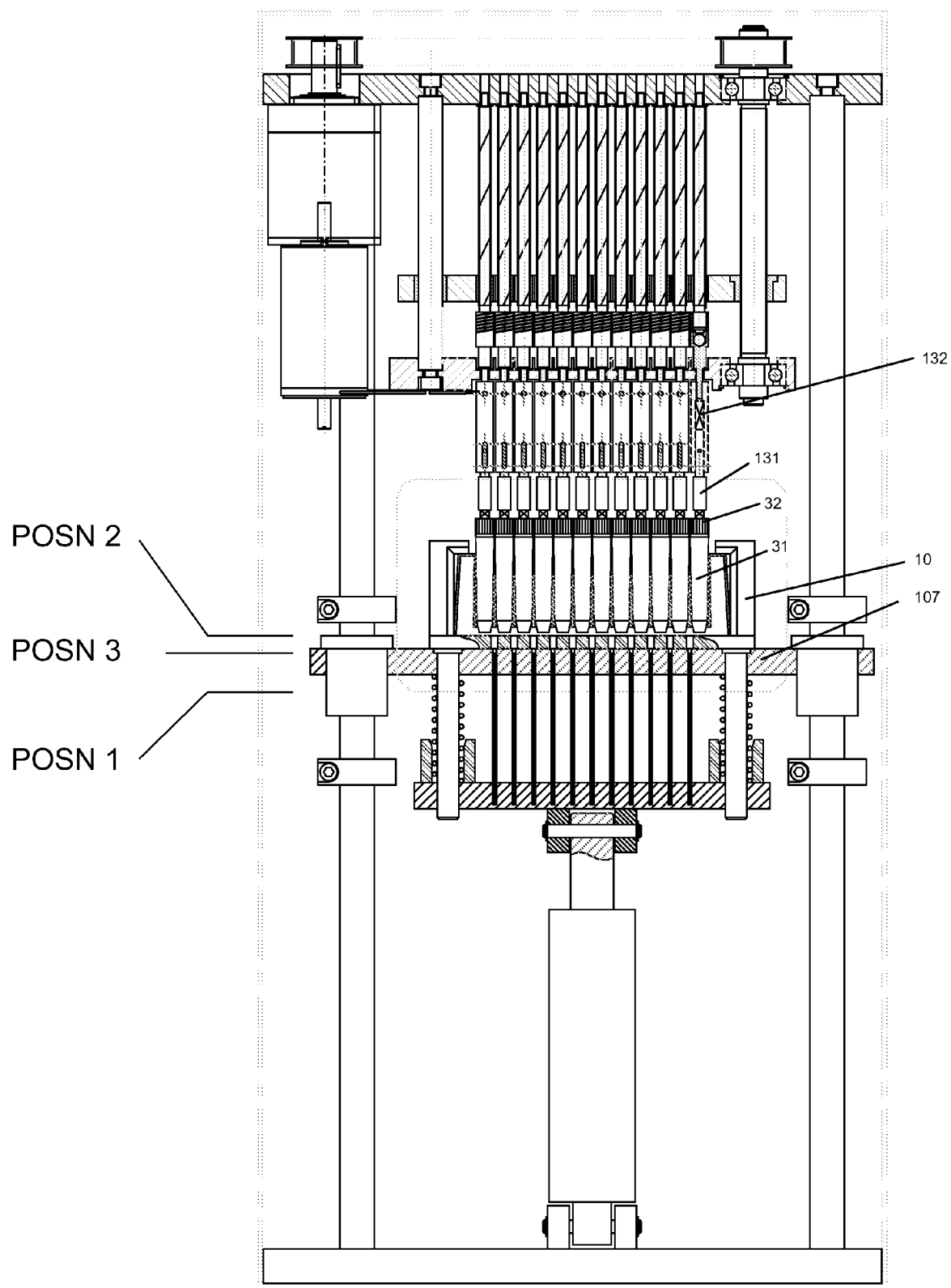
Figure 4:
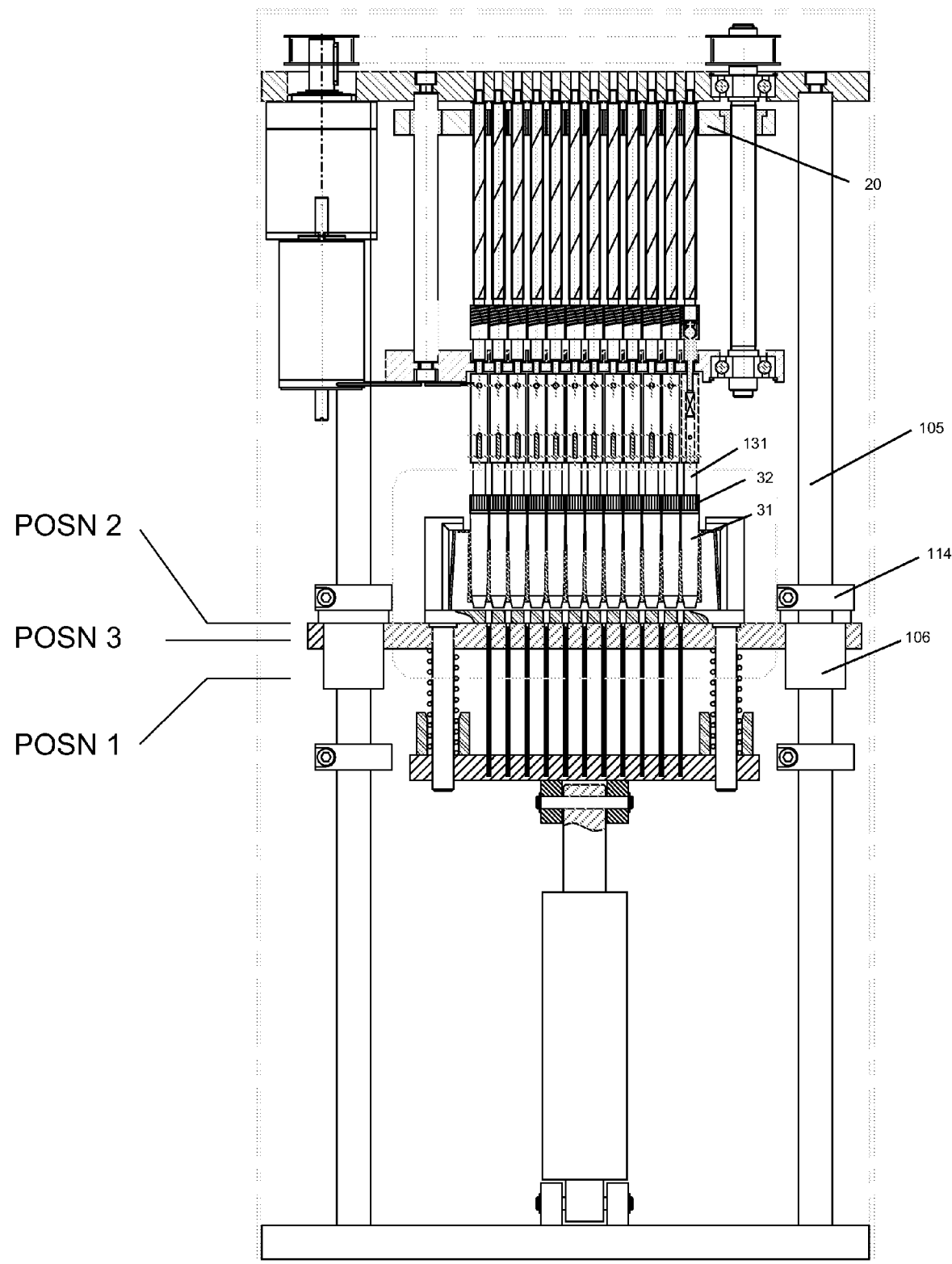

After insertion of the rack 11 into the rack support 10, the operator initiates a de-capping sequence which causes the actuator 108 to lift the rack support 10 to the position POSN3 as shown in FIG. 3 until the caps 32 of the tubes 31 engage the bottom of the drive spigots 131 and start to compress the springs 132 in each of the drive spindles 13. The spindles 13 are rotated during this process in a clockwise direction (when viewed from above) by upwards movement of the drive plate 20 so that, as the rack support continues to move upwards to the position POSN2 as shown in FIG. 4, the spigots 131 engage in sockets (not shown) in the caps 32. Not all of the caps 32 will be engaged by their respective spigots 131 at the same time and some of the spindles 13 will be compressed against the action of the springs 132 until the drive spigots align rotationally with the cap sockets, to ensure that all the caps 32 are located on respective spigots 131. The clutches 133 allow a short period of overrun to be accommodated within those spindles whose drive spigots 131 engage first. The position POSN2 is defined by stop collars 114 on the shafts 105 which prevent further upward movement of the rack support 10 by engagement with the upper ends of the sliding bearings 106. The springs 132 are now compressed and the tubes 31 are prevented from upwards movement by the engagement of the caps 32 with the drive spigots 131.

Figure 5:
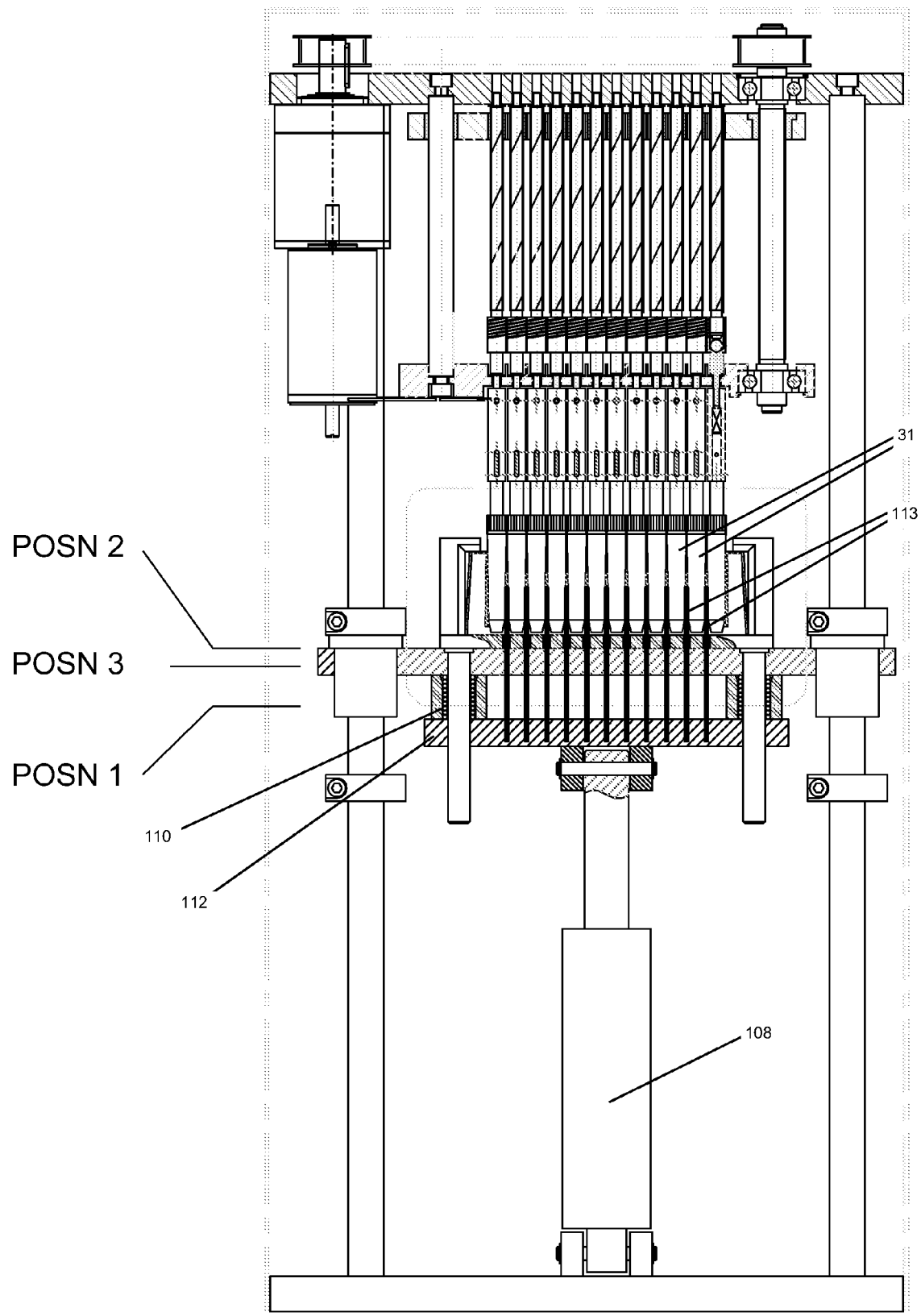
Figure 6:
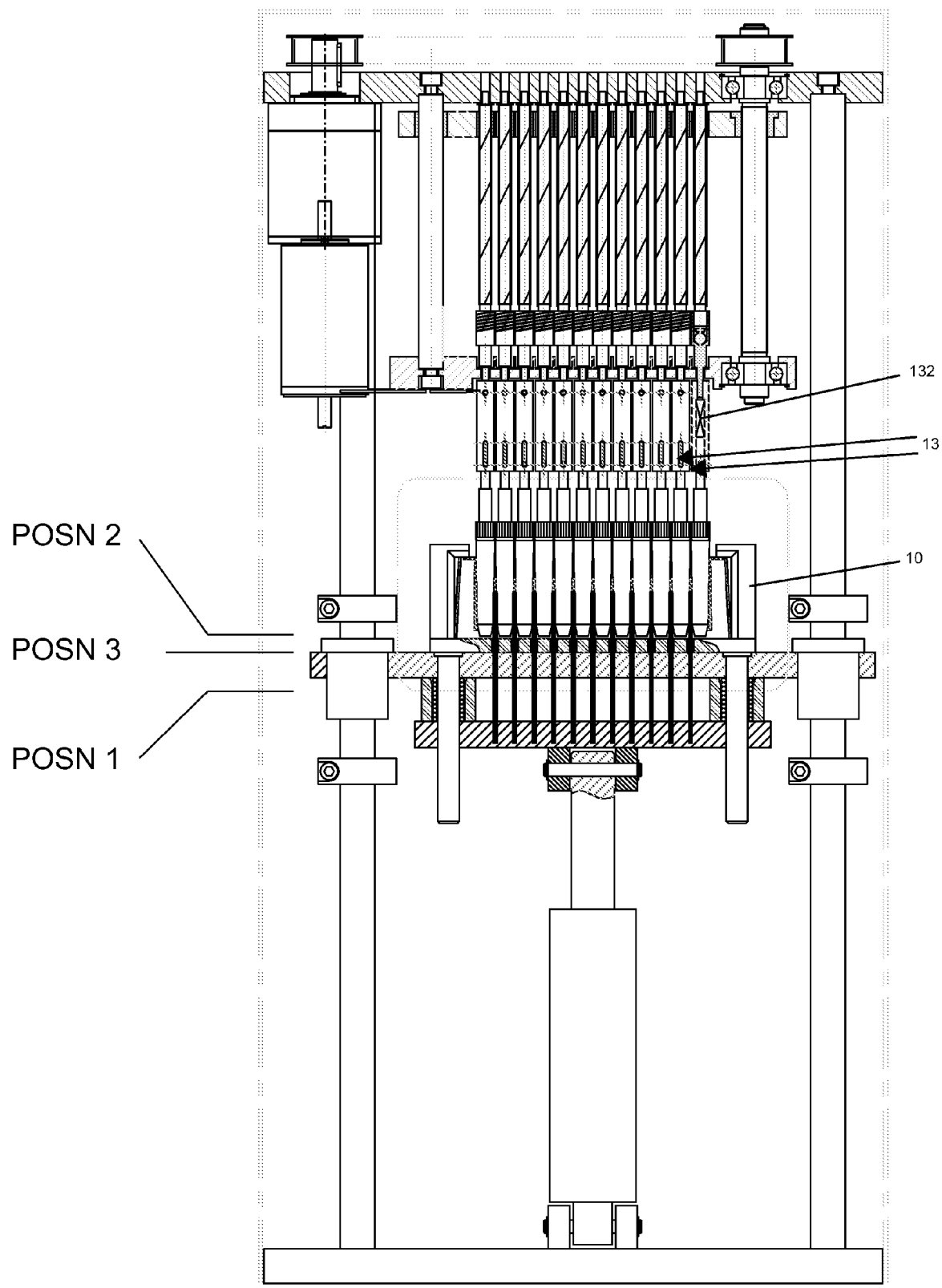
Figure 7:
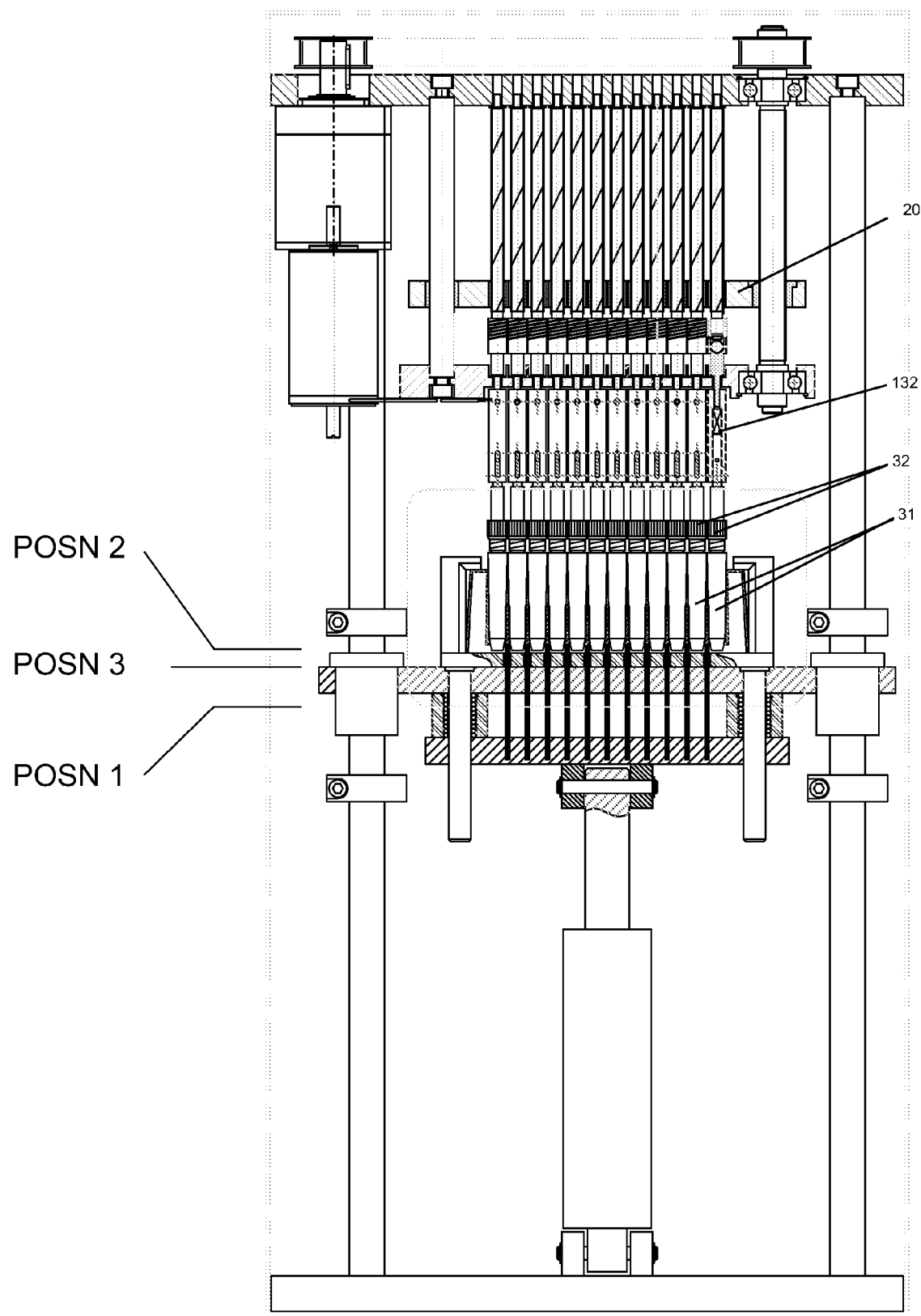

The actuator 108 continues to lift the secondary drive plate 112 which causes compression of the springs 110 and inserts the locking pins 113 through the apertures 104 and into locking engagement between the sides of the tubes 31 as shown in FIG. 5. The tubes are now locked in place and the rack support 10 is lowered to the position POSN3 as shown in FIG. 6, allowing the spindles 13 to extend under the action of the springs 132, and the spindles 13 are then rotated anti-clockwise as the drive plate 20 is lowered, to unscrew the caps 32 from their respective tubes 31 as shown in FIG. 7, the clutches 133 tightening up to overcome any resistance to de-capping. As this occurs the spindle springs 132 accommodate the upwards movement caused by the unscrewing of the caps 32.

Figure 8:
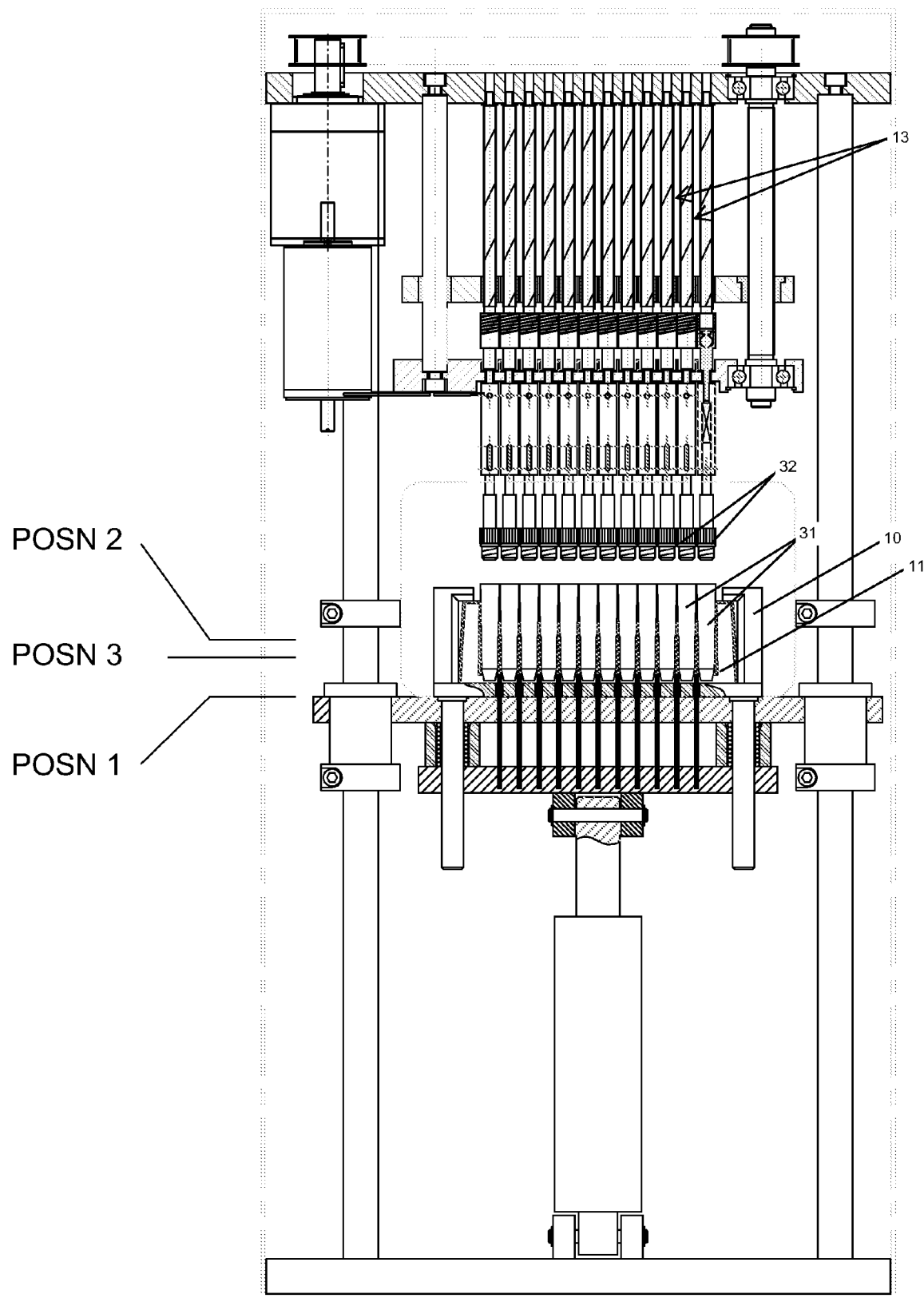
Figure 9:
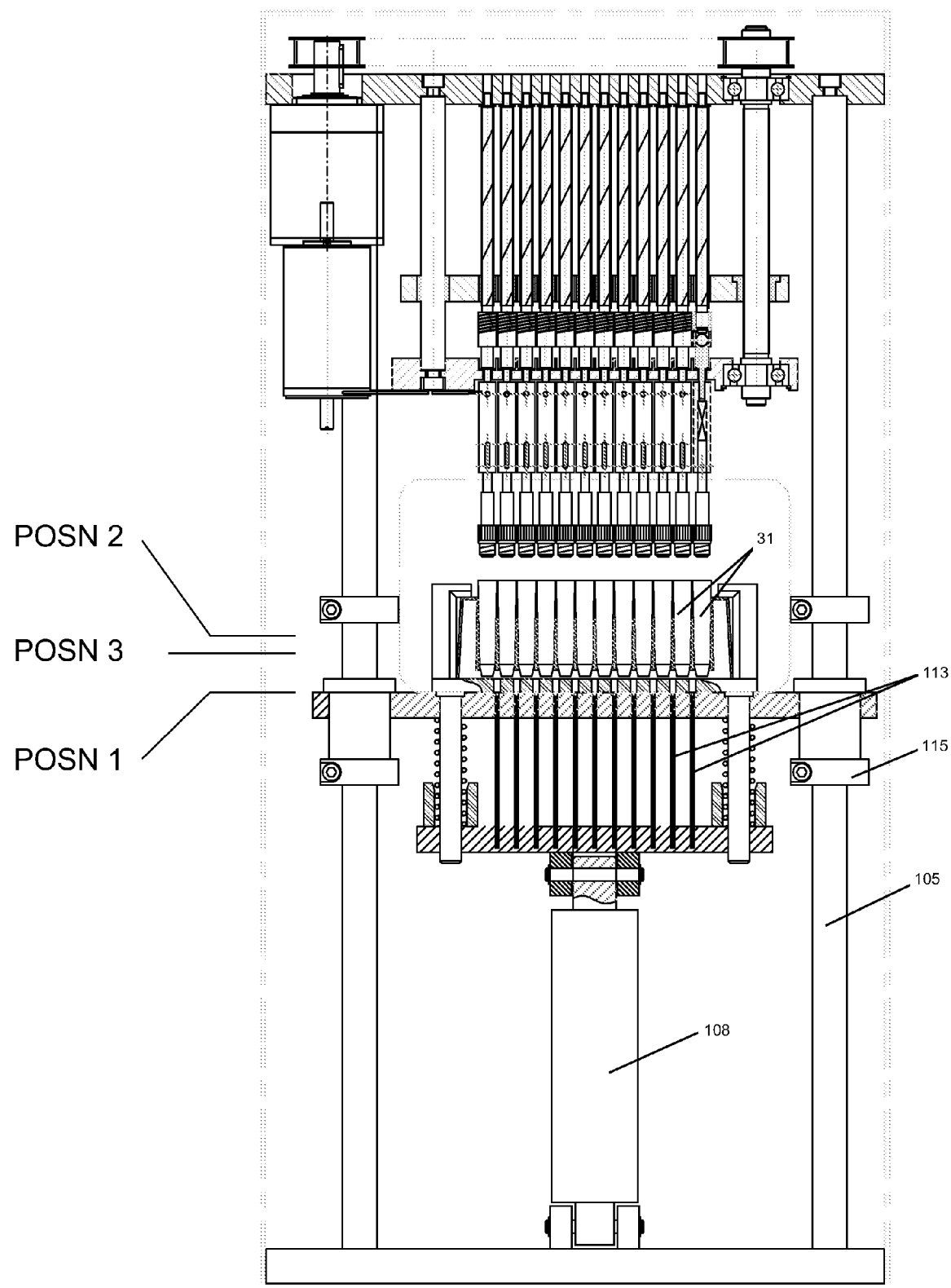

The rack support 10 is then lowered to the position POSN1 as shown in FIG. 8, the caps 32 being retained on the spindles 13 as the tubes 31 are lowered in the rack 11 on the rack support 10. The rack support 10 is lowered to the position POSN1 defined by the collars 115 on the shafts 105 engaging the sliding bearings 106. The actuator 108 is the fully retracted, disengaging the tube-locking pins 113 from the tubes 31 as shown in FIG. 9. A drip tray (not shown for clarity) may be slid automatically into position between the bottom of the caps 32 and the tops of the tubes 31 to prevent cross-contamination from droplets from one cap 32 dropping onto a tube other than that from which it has been removed.

At this point the rack 11 with its associated tubes 31 can be removed by the operator for processing. For example further samples or active components may require to be inserted into the tubes 31 depending upon the particular process operating.

Figure 10:
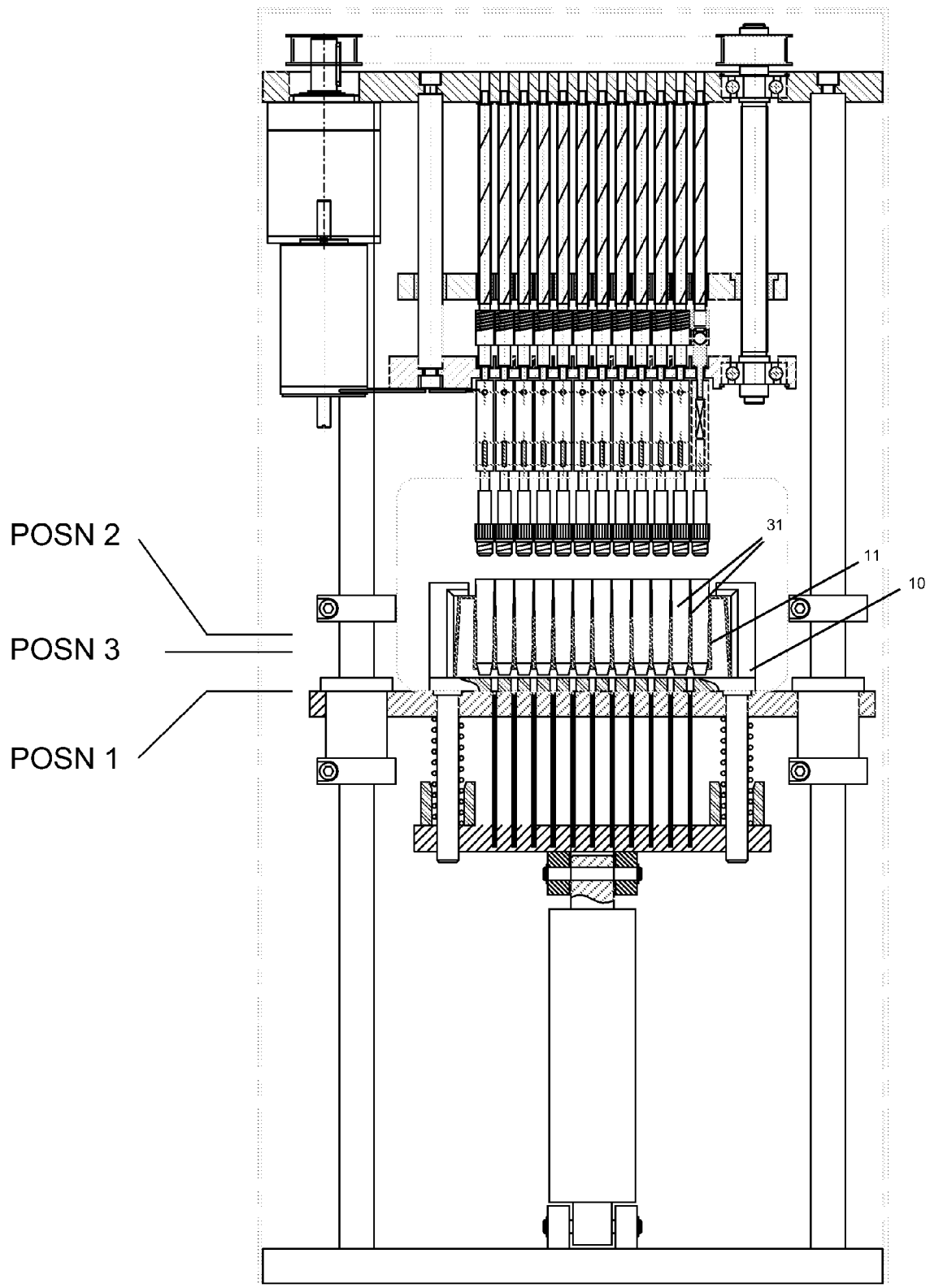
Figure 11:
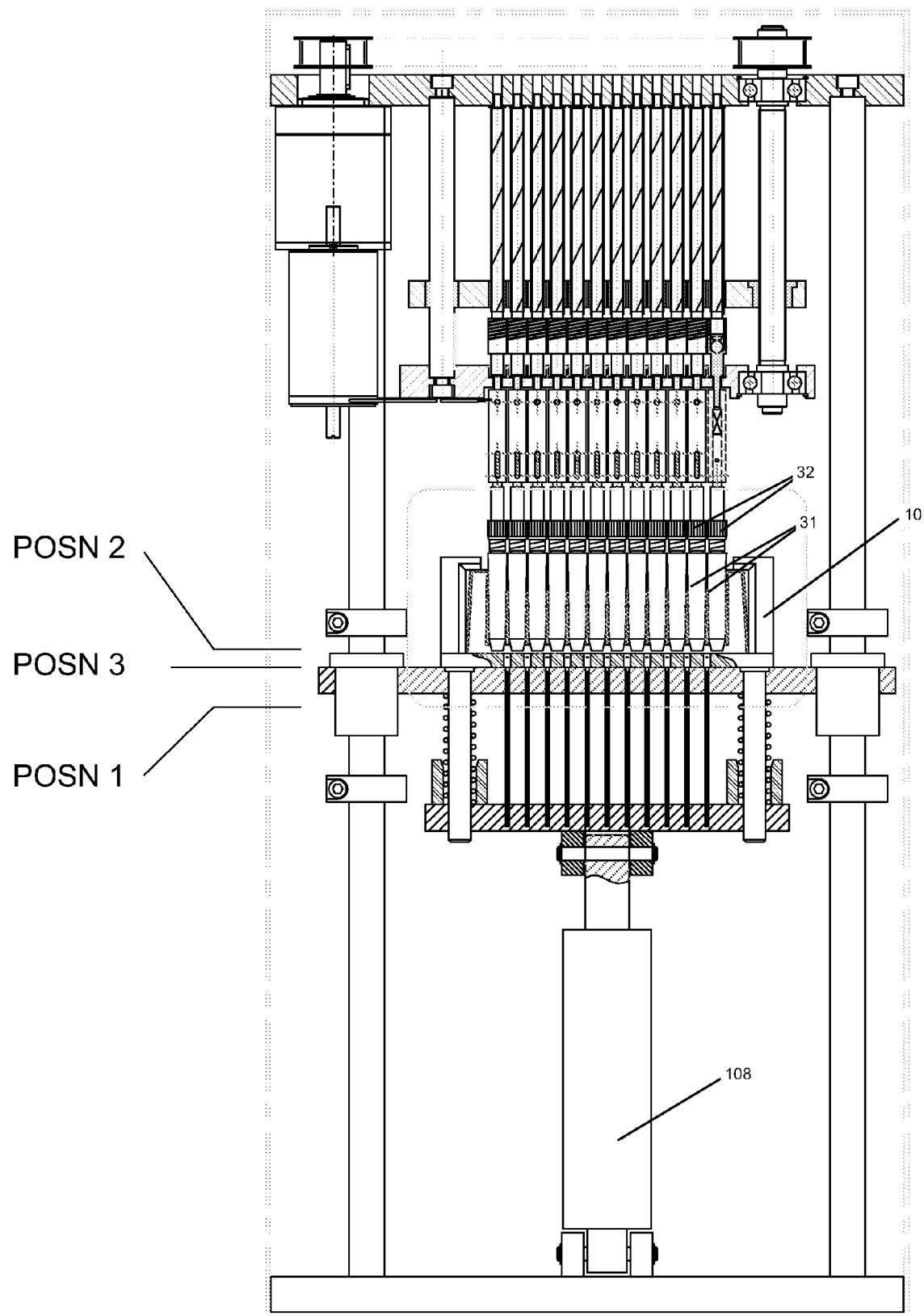
Figure 12:
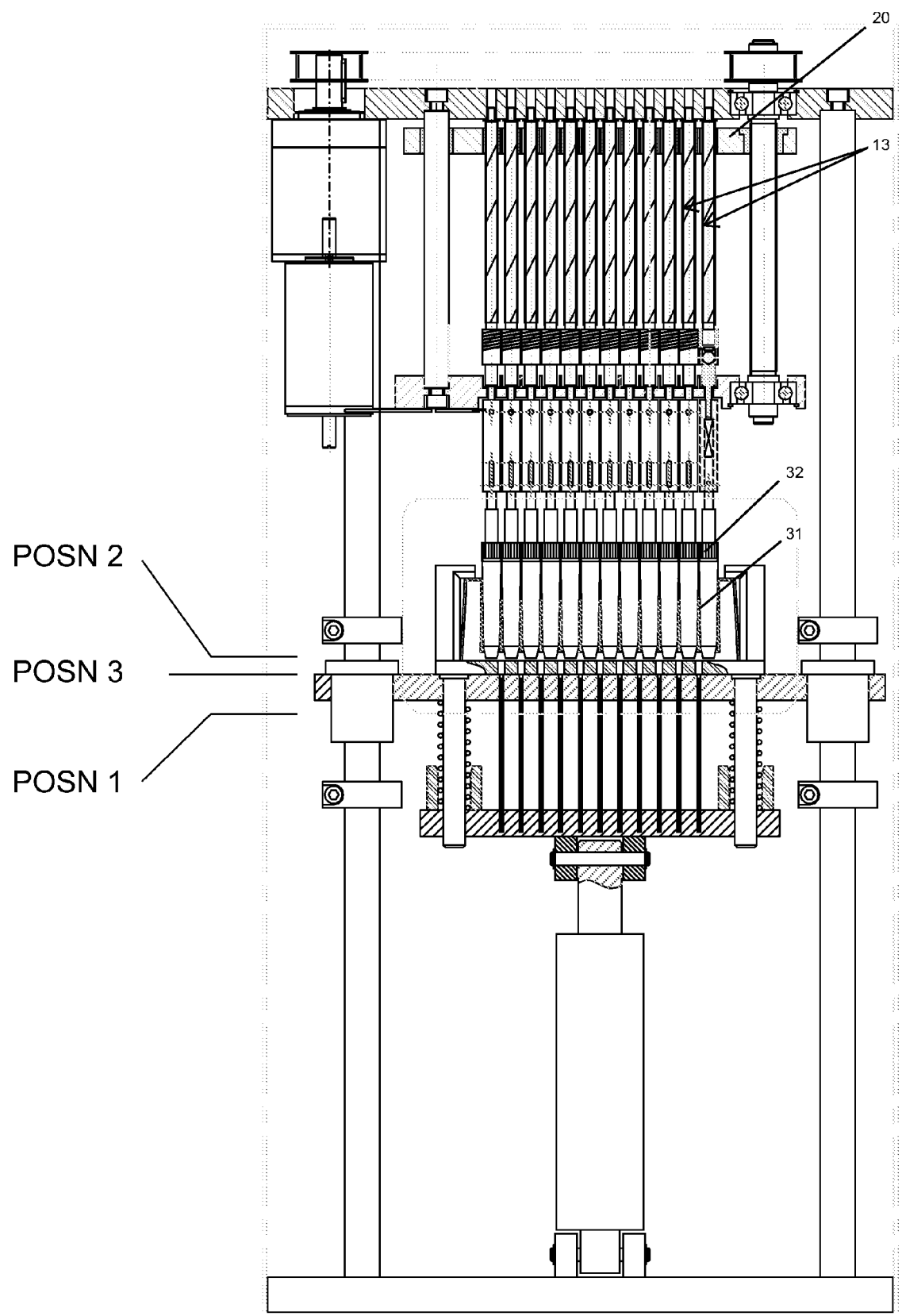
Figure 13:
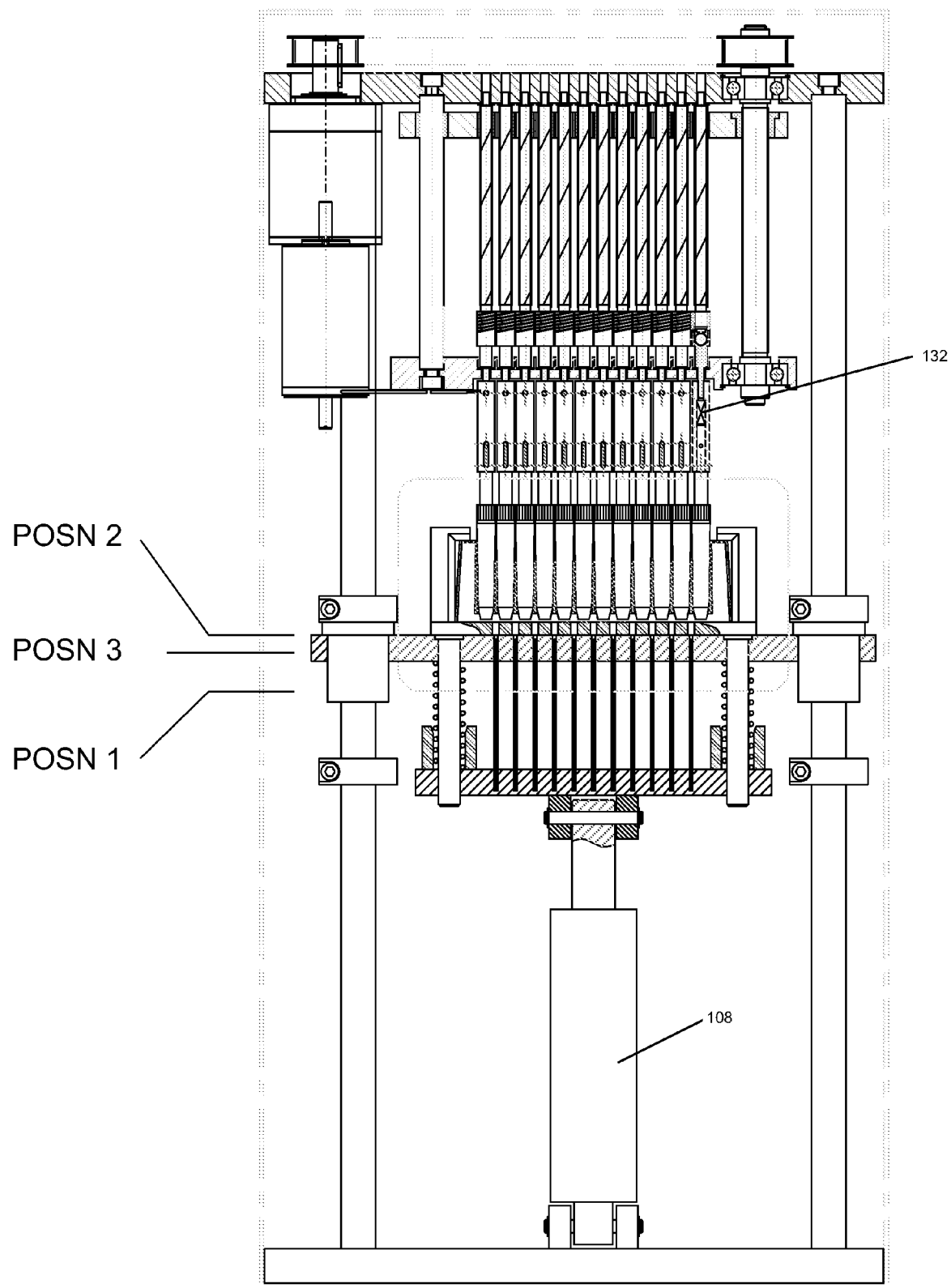
Figure 14:
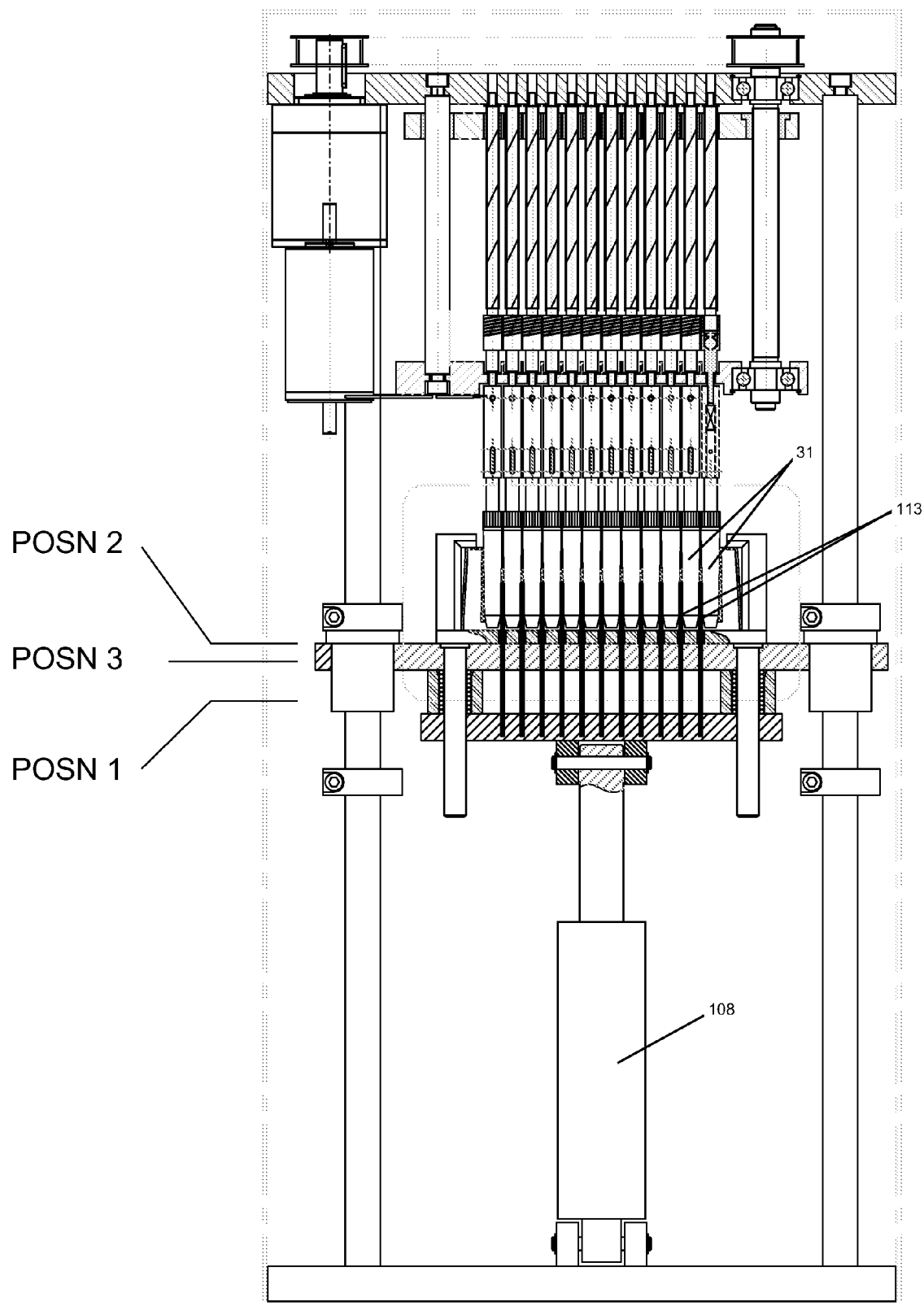

FIG. 10 shows the start of a capping cycle in which a rack 11 of uncapped tubes 31 is inserted in the rack support 10. The actuator 108 is operated as shown in FIG. 11 to move the rack support 10 to the position POSN3 so that the caps 32 retained on the spindles 13 engage with the top of the tubes 31. The spindles 13 are then rotated clockwise by upwards movement of the drive plate 20, re-capping the tubes 31 (see FIG. 12), individually, to the desired torque as discussed above. As this proceeds the actuator 108 lifts the rack support 10 to the POSN2 compressing the spindle springs 132 (see FIG. 13) and the actuator 108 continues to move upwards in order to insert the locking pins 113 through the apertures 104 and into engagement with the tubes 31 as shown in FIG. 14.

Figure 15:
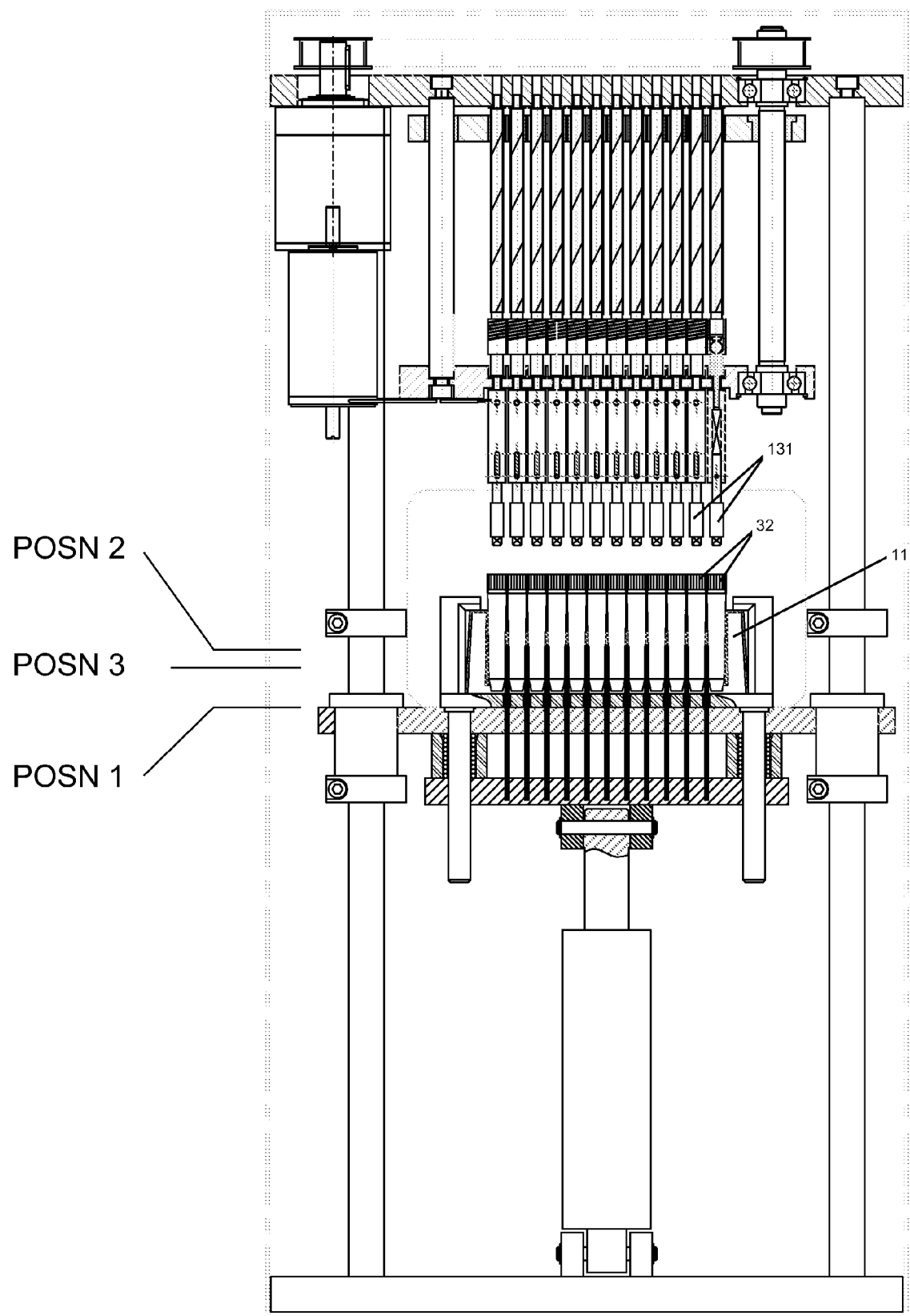
Figure 16:
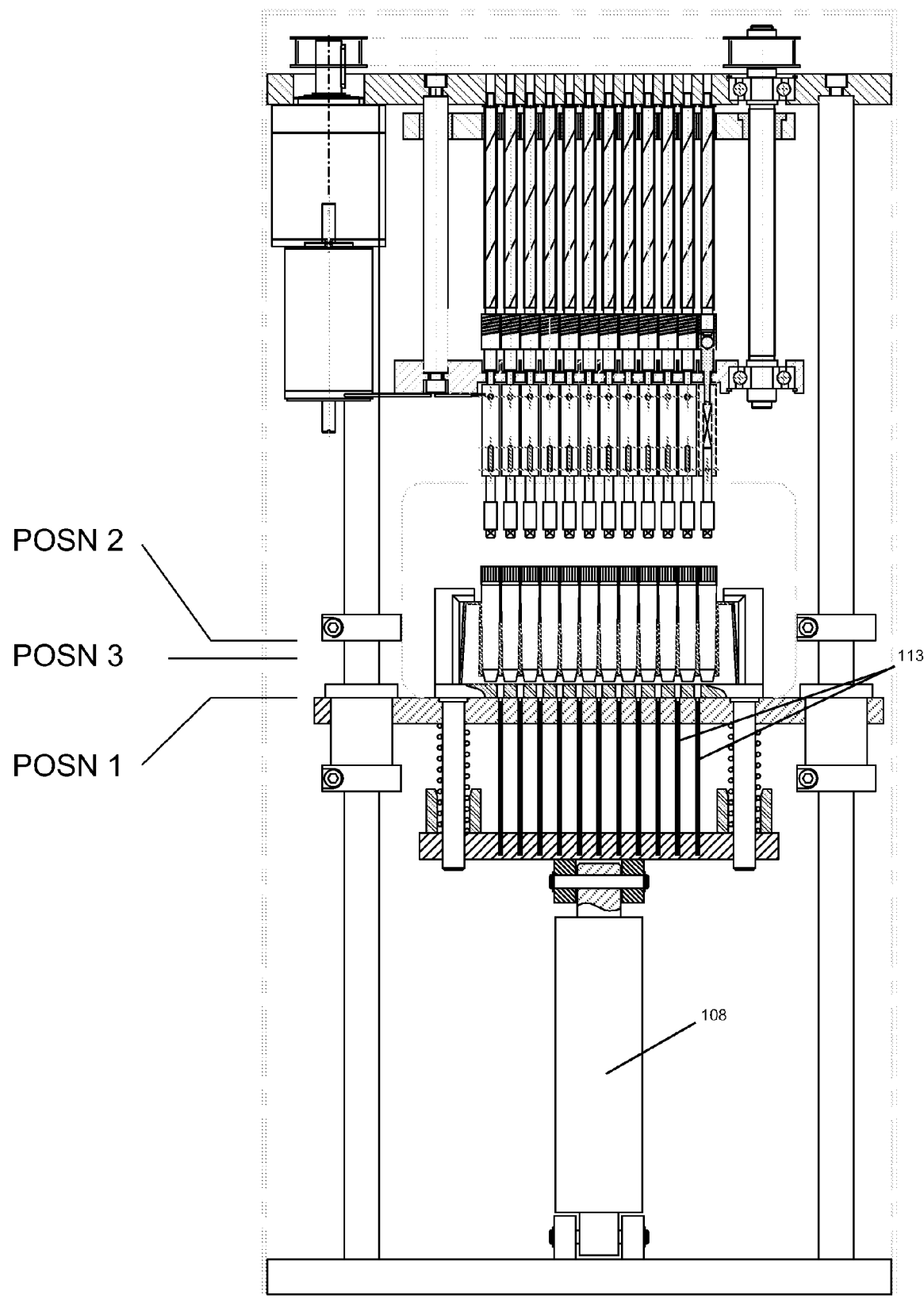
Figure 17:
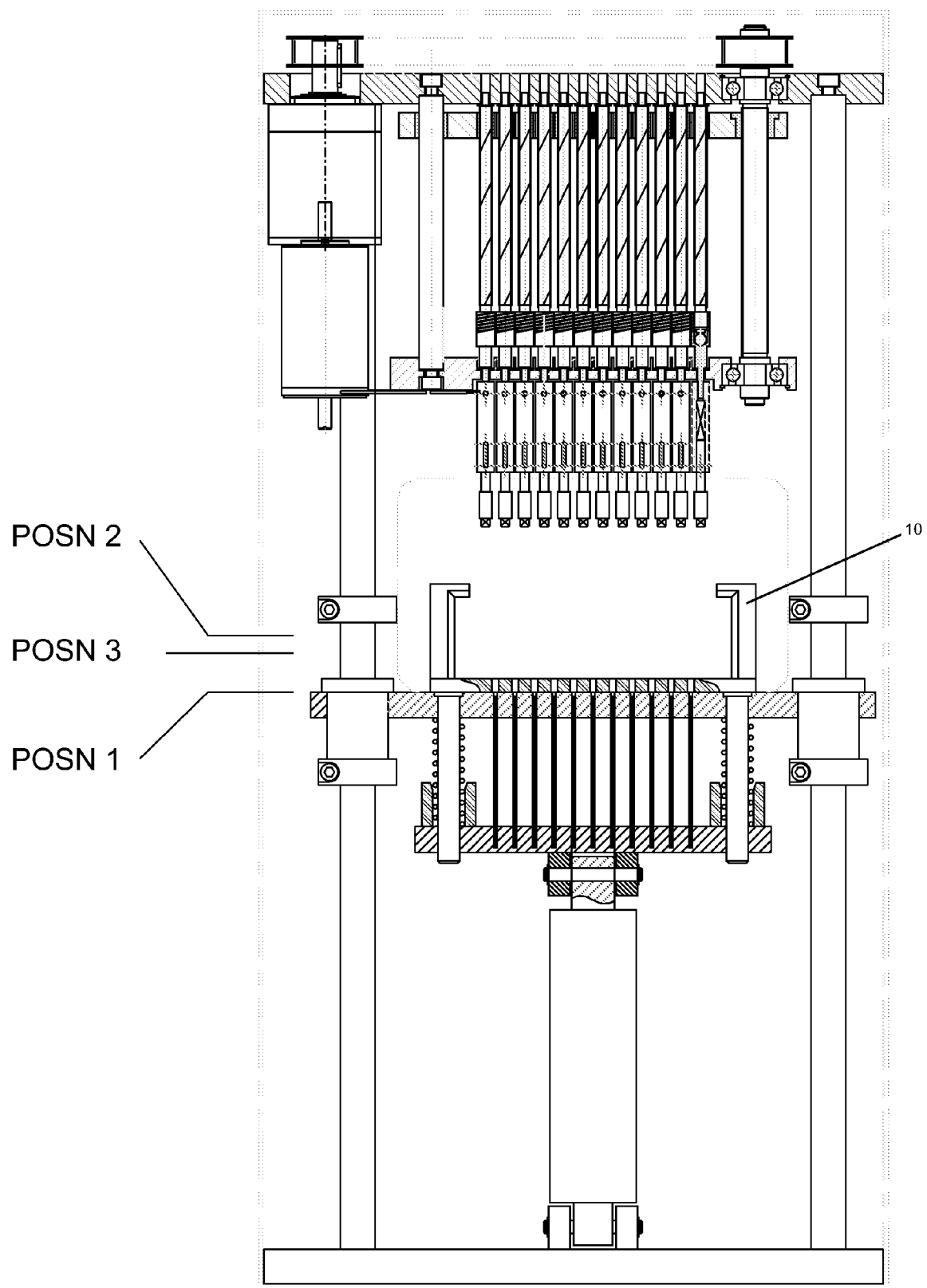

In the next step, see FIG. 15, the rack support is lowered to the position POSN1, removing the spigots 131 from the caps 32, the tubes 31 being held within the rack 11 by means of the locking pins 113, and thereafter, see FIG. 16, the actuator 108 is fully retracted, withdrawing the locking pins 113 and leaving the rack 11 (of now capped tubes 31) to be removed (see FIG. 17).

FIG. 18 shows a pair of adjacent spindles, one partially sectioned, in further detail.

Figure 19:
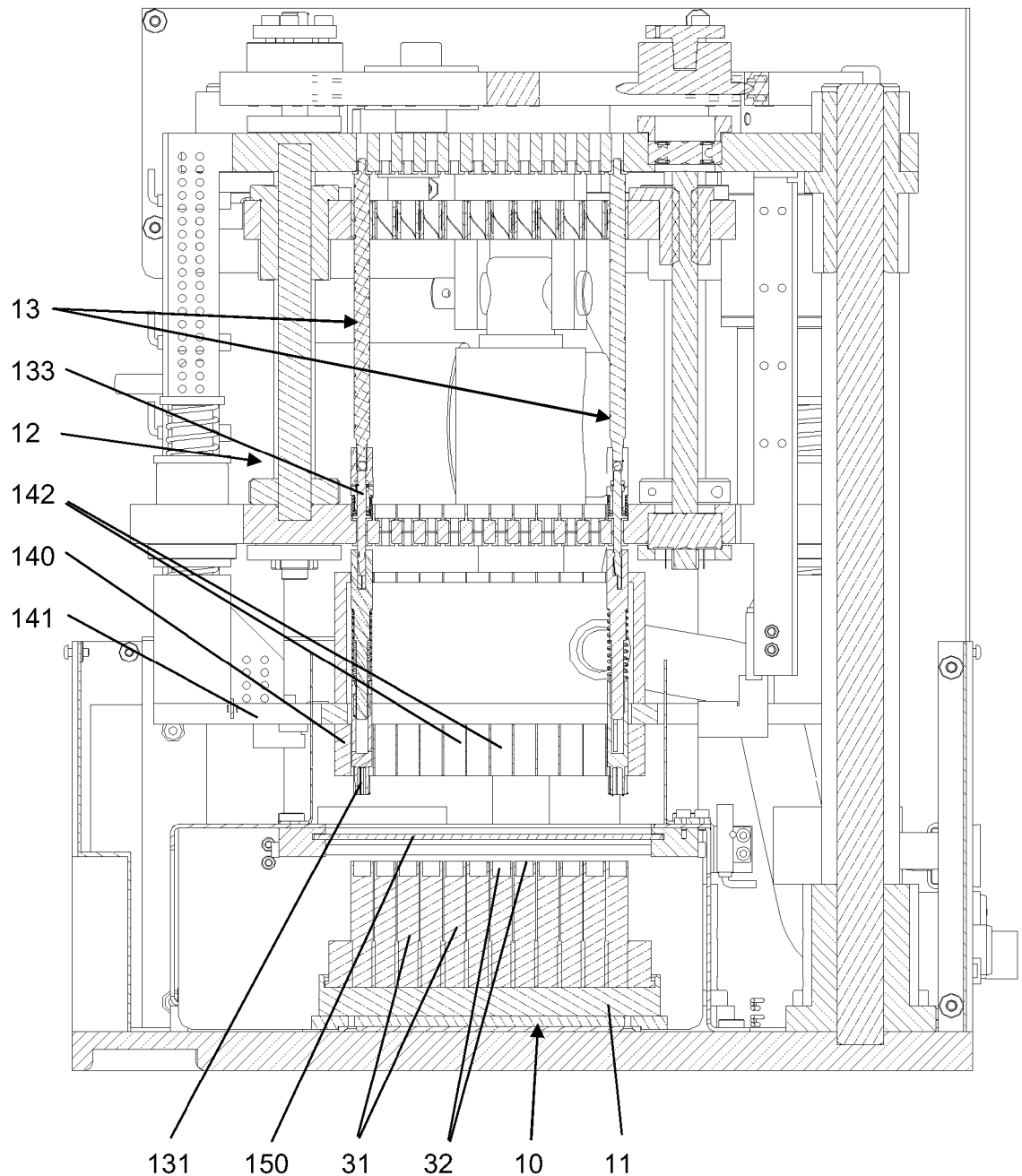
FIG. 19 shows an elevation of a second example.

FIG. 19 shows a second example with the same components being identified with the same reference numerals for simplicity, and in which the primary difference is that, instead of the rack support 10 being movable vertically as in the example shown in FIGS. 1 to 17, the rack support is in a fixed position and all the vertical relative movement between the rack and the head unit 12 takes place by movement of the head unit 12.

Further differences are that the drive plate 112 and locking pins are dispensed with in the second example and to hold the tubes 31 within the corresponding rack 11 during disconnection of the capper/de-capper spigots 131 on the drive spindles 13 from the tube caps 32, a stripper plate 140 is provided which can be moved downwardly into position when required, with the head unit 12 and which can be held in place by electromagnetic clamps (not shown) disposed beneath a stripper plate support plate 141. The stripper plate 140 has bores 142 which are aligned with and through which extend the lower parts of the drive spindles 13, the diameter of each of the bores being less then the diameter of the tube caps 32. The stripper plate 140 is thus arranged to engage the tops of the tube caps 32 in use to prevent the tubes from 31 being lifted out of the rack 11 when the capper/de-capper spigots 131 are moved away from the rack to disengage from the tubes.

FIG. 19 shows the head unit in a raised position and in this position a drip tray 150 is shown disposed beneath the bottom of the capper/de-capper spigots 131 so that, when caps 32 have been removed, the drip tray can be moved transversely into position beneath the caps held on the spigots 131 to catch an liquid droplets which would otherwise fall into the tubes or, when the rack has been removed, on to the base of the apparatus.

A further difference lies in the use of ramp clutches 133 instead of the spring wrap clutches used in the first example.

It will be appreciated that specific details of the system may be altered without departing from the concept of the invention.

The invention claimed is:

1. A capper/de-capper system comprising:
   a rack support for supporting a rack containing a plurality of capped tubes in a given position;
   a head unit supporting a two-dimensional array of capping/de-capping spindles, each including a clutch and a capping/de-capping spigot or socket, the spindles being aligned with the tube positions defined in the rack;
   a drive mechanism for moving the tubes and head unit relatively towards and away from one another in use, when a rack containing capped tubes is disposed in the rack support, to cause engagement and disengagement of the capping/de-capping spigots or sockets with and from the tube caps; and
   a spindle drive system for causing simultaneous rotation of the capping/de-capping spindles and rotation of the capping/de-capping spigots or sockets, said rotation of the capping/de-capping spigots or sockets after engagement of the capping/de-capping spigots or sockets with the caps, causing either attachment of the caps to the tubes when the spindles rotate in the one direction or detachment of the caps from the tubes when the spindles rotate in the other direction, wherein
   each capping/de-capping spindle includes a clutch arranged to slip in the one direction when a desired given torque is exceeded, said clutches being arranged to apply a higher torque when the spindles rotate in the other direction to de-cap the tubes than when rotating in the one direction to cap the tubes and tighten each cap to the desired given torque.

2. A capper/de-capper according to claim 1, including means for moving the tubes towards or away from the head unit.

3. A capper/de-capper according to claim 2, including means for driving wherein the rack support upwardly and downwardly.

4. A capper/de-capper according to claim 1, including means for moving the head unit towards or away from the tubes.

5. A capper/de-capper according to claim 1, wherein the spindle drive system includes a drive plate movable upwardly and downwardly with respect to the spindles and in screw-threaded engagement therewith, and means for moving the drive plate upwardly or downwardly, to cause simultaneous rotation of the spindles on movement of the drive plate relative thereto.

6. A capper/de-capper according to claim 1, wherein the spindle drive system includes a plurality of gear wheels in driving engagement with the spindles.

7. A capper/de-capper according to claim 1, wherein the spindle drive system includes a plurality of rack and pinion drives, each spindle having a pinion mounted or formed thereon.

8. A capper/de-capper according to claim 1, wherein the spindle drive system includes a plurality of pulleys and one or more belts driving the pulleys.

9. A capper/de-capper according to claim 1, wherein the clutch on each spindle comprises a spring-wrap clutch.

10. A capper/de-capper according to claim 1, wherein the clutch on each spindle comprises a pair of toothed dogs arranged to slip in the one direction when the torque exceeds a given limit overcoming the spring-loading.

11. A capper/de-capper according to claim 1, wherein the rack support includes a plurality of locking pins engageable with individual ones of the tubes in a rack in use, to hold the tubes in fixed position within the rack.

12. A capper/de-capper according to claim 11, wherein the locking pins are engageable upwardly through the rack support and rack into engagement with the tubes.

13. A capper/de-capper according to claim 1, wherein each of the drive spigots or sockets is arranged to be movable axially under spring action to accommodate misalignment with a respective cap until the spindle and spigot or socket have rotated sufficiently to enable engagement with the cap.

14. A capper/de-capper according to claim 1, further including a stripper plate having a plurality of apertures corresponding to positions of the tubes, through which a lower end of the capping/de-capping spigots or sockets extend, each of which spigots or sockets is withdrawn upwardly through the corresponding aperture in order to disengage from the respective tube cap, to prevent the tubes from being lifted out of the rack when the capping/de-capping spigots or sockets are moved away from the rack to disengage from the tubes.

* * * * *